United States Patent [19]

Deckner et al.

[11] Patent Number: 4,604,281

[45] Date of Patent: Aug. 5, 1986

[54] COSMETIC AND SKIN TREATMENT COMPOSITIONS CONTAINING ACETYLATED STEROLS

[75] Inventors: George E. Deckner, Westfield; Clara G. Mercado, Aberdeen; Ann M. Krog, Eatontown, all of N.J.

[73] Assignee: Charles of the Ritz Group Ltd., New York, N.Y.

[21] Appl. No.: 646,409

[22] Filed: Sep. 4, 1984

Related U.S. Application Data

[63] Continuation-in-part of Ser. No. 477,562, Mar. 21, 1983, abandoned.

[51] Int. Cl.$^4$ .................... A61K 7/42; A61K 7/021; A61K 47/00
[52] U.S. Cl. ...................................... 424/59; 424/60; 424/63; 514/844; 514/845; 514/847
[58] Field of Search .................. 424/59, 60, 63, 358, 424/365; 514/844, 845, 847

[56] References Cited

U.S. PATENT DOCUMENTS

| | | | |
|---|---|---|---|
| 4,218,334 | 8/1980 | Lundmark | 424/172 X |
| 4,393,044 | 7/1983 | Takada et al. | 424/59 |

FOREIGN PATENT DOCUMENTS

| | | | |
|---|---|---|---|
| 1540187 | 9/1968 | France | 424/59 |
| 52-79030 | 7/1977 | Japan . | |
| 794018 | 1/1981 | U.S.S.R. | 424/358 |

OTHER PUBLICATIONS

"Generol ® 122", Cosmedia, Dept. of General Mills Chemicals, Inc., Minneapolis.
Chem. Abs. 88: 197435s (1978).
Chem. Abs. 97: 203100h (1982).
Chem. Abs. 97: 28414q (1982).

*Primary Examiner*—Sidney Marantz
*Assistant Examiner*—Shawn P. Foley
*Attorney, Agent, or Firm*—Lawrence S. Levinson; Burton Rodney

[57] ABSTRACT

Cosmetic and skin treatment compositions are provided which include as emollients acetylated soy bean derived sterols, namely, acetylated sitosterol, acetylated campesterol, and/or acetylated stigmasterol. The above-acetylated sterols impart improved hand feel and barrier properties to the compositions, are naturally compatible with skin and have improved skin penetration properties over unesterified sterols.

9 Claims, No Drawings

COSMETIC AND SKIN TREATMENT COMPOSITIONS CONTAINING ACETYLATED STEROLS

REFERENCE TO OTHER APPLICATIONS

This application is a continuation-in-part of application Ser. No. 477,562, filed Mar. 21, 1983, now abandoned.

FIELD OF THE INVENTION

The present invention relates to cosmetic and skin treatment compositions which contain acetylated soya bean derived sterols, also referred to as acetylated phytosterols.

BACKGROUND OF THE INVENTION

Phytosterol is obtained from edible soybean oil and is essentially a uniform blend of plant sterols comprised primarily of sitosterol, campesterol and stigmasterol (available as Generol 122, Cosmedia, Dept. of General Mills Chemicals, Inc. Minneapolis). When employed in cosmetic and toiletry formulations, phystosterol apparently acts as auxiliary and primary emulsifier, emollient, consistency modifier and emulsion stabilizer. It has been suggested that phytosterol be employed as an auxiliary emulsifier in borax-beeswax cold cream formulations to promote water-in-oil emulsions. In addition, it has been suggested that phytosterol with its water absorbing capability in hydrophobic bases be used in protective water-absorbable ointment bases. The phytosterol apparently will act as a consistency modifier and emulsion stabilizer in typical oil-in-water emulsions of the triethanolamine sterate type. In addition, it has been suggested that the emollient and skin penetrating properties of soy sterols will impart a more supple condition to the skin. Furthermore, phytosterol has apparently been found to enhance gloss as well as contribute just a hint of creamy gel-like elegance to many skin care emulsion products.

BRIEF DESCRIPTION OF THE INVENTION

It has now surprisingly been found that cosmetic and skin care formulations containing acetylated phytosterol, that is, a blend of acetylated sitosterol, acetylated campesterol and acetylated stigmasterol, and which is exclusive of acetylated cholesterol or other cholesterol esters, have substantially improved properties over similar cosmetic and skin care formulations containing the natural unesterified phytosterol. It has been found that acetylated phytosterol when employed in cosmetic, toiletry and skin care formulations acts as an emollient but unlike the unesterified phytosterol does not act as an auxiliary and primary emulsifer, consistency modifier, viscosity modifier or emulsion stabilizer.

In fact, it has been found that the acetylated phytosterols employed herein, as compared to the unesterified phytosterol and esterified and unesterified cholesterol, have improved hand feel and skin penetrability. In addition, the acetylated phytosterols employed herein, as compared to unesterified phytosterol have improved barrier and moisturizing properties (that is, improved occlusivity of formed skin film to provide reduced skin moisture loss), are naturally compatible with skin in that they are similar to sterol esters (for example, cholesterol esters) found in the skin, and have improved solubility in oils to provide the feel of a wax without excessive body thickness or viscosity. Accordingly, cosmetic and skin care formulations containing the acetylated phytosterol will be superior in the above respects to similar formulations containing the unesterified phytosterol.

DETAILED DESCRIPTION OF THE INVENTION

In accordance with the present invention, there is provided improved cosmetic and skin care and treatment compositions which contain as an essential ingredient one or more acetylated soya bean derived sterols (also referred to herein as acetylated sterols), which does not include acetylated cholesterol, and preferably one or more of acetylated sitosterol, acetylated campesterol, acetylated stigmasterol, and more preferably a uniform blend of the above acetylated sterols, also referred to as acetylated phytosterol. The acetylated soya bean derived sterols impart to the cosmetic and skin care and treatment compositions improved feel and barrier properties (which leads to improved moisturizing properties) as well as improved skin penetrability.

The cosmetic formulations and skin care and treatment formulations of the invention will contain from about 0.3 to 4% and preferably from about 1 to about 2% by weight of acetylated sterols. As indicated, the acetylated sterols may include any of those derived from soya bean oil and will preferably comprise a sterol blend containing from about 40 to about 80% and preferably from about 50 to about 60% by weight acetylated sitosterol based on the total weight of the sterol blend, from about 10 to about 40% and preferably from about 20 to about 30% by weight acetylated campesterol based on the total weight of the sterol blend, and from about 1 to about 20% and preferably from about 1 to about 5% by weight stigmasterol based on the total weight of the sterol blend. Thus, the acetylated sitosterol will preferably be employed in a weight ratio to the campesterol of within the range of from about 2:1 to about 4:1 and more preferably from about 2:1 to about 2.5:1, and the acetylated sitosterol will preferably be employed in a weight ratio to the stigmasterol of within the range of from about 4:1 to about 40:1 and more preferably from about 16:1 to about 40:1.

Where the formulation of the invention is a make-up or cosmetic formulation, it will contain the acetylated sterol in an amount within the range of from about 0.1 to about 10% by weight and preferably from about 1 to about 2% by weight.

Where the formulation of the invention is a skin care or treatment formulation such as a protective daytime lotion or moisturizer, body oil, bath oil or sunscreen emulsion, the acetylated sterol will be present in an amount within the range of from about 1 to about 10% by weight and preferably from about 1 to about 2% by weight.

The cosmetic and skin treatment formulations of the invention will also contain conventional cosmetic ingredients necessary in formulating a desirable product, such as, one or more diluents, thickeners, stabilizers, coloring agents, humectants, preservatives, emollients, bodying agents, sunscreen agents and the like. Thus, the formulations of the invention may contain one or more diluents such as deionized water in an amount within the range of from about 40 to about 90% and preferably from about 50 to about 80% by weight, optionally one or more thickeners, such as magnesium aluminum silicate and xanthan gum in an amount within the range of from about 0.1 to about 2% and preferably from about 0.5 to about 1% by weight, in the case of cosmetic or make-up formulations one or more coloring agents or pigments such as titanium dioxide, various ion oxides, ultramarine blue and the like totaling from about 10 to about 15% by weight, skin protecting agents, such as panthenol, which serves as a skin moisturizer and humectant, in an amount within the range of from about 0.1 to about 5% and preferably from about 0.1 to about 1% by weight, one or more other humectants such as polyethylene glycols (for example, Carbowax 400), sodium 2-pyrrolidone carboxylic acid, sorbitol, propylene glycol or glycerine in an amount within the range of from about 1 to about 20% and preferably from about 1 to about 5% by weight, one or more preservatives such as parabens including methyl paraben, propyl paraben, butyl paraben, Glydant (dimethyldimethoyl hydantoin), benzyl alcohol, imidazolidinyl urea and the like usually employed in amounts within the range of from about 0.1 to about 1% by weight and preferably from about 0.5 to about 0.8% by weight, one or more emollients or emollient oils such as petrolatum, propylene glycol dicaprylate/dicaprate, and diisopropyl dimerate in an amount within the range of from about 10 to about 20% by weight and preferably from about 10 to about 15% by weight, one or more emulsifiers such as PEG 20 sorbitan monolaurate (Polysorbate 20), diethanolamine cetyl phosphate, glyceryl stearate, polyethylene glycol 100 stearate, and PEG 20 stearyl ether (Brij 78, Steareth 20) in an amount within the range of from about 0.5 to about 10% by weight and preferably from about 1 to about 3% by weight; one or more bodying agents (opacifier) such as stearic acid, glyceryl monostearate, and the like in an amount within the range of from about 1 to about 10% by weight and preferably from about 1 to about 5% by weight, optionally one or more sun screen agents such as octy dimethyl p-aminobenzoic acid, benzophenone 3 and the like in an amount within the range of from about 0.5 to about 10% by weight and preferably from about 1 to about 5% by weight, and optionally one or more antioxidants such as dl-alpha-tocopherol in an amount within the range of from about 0.05 to about 0.5% by weight and preferably from about 0.05 to about 0.2% by weight. In addition, the formulations of the invention may contain one or more fragrances, solubilizing agents and emulsifiers for the fragrances such as polyoxyethylene (13) octyl phenyl ether.

The cosmetic formulation of the invention may be prepared as follows.

Deionized water (diluent) together with thickener/-stabilizer such as magnesium aluminum silicate are mixed together to form a first mixture (A). Coloring agents or pigments are mixed therewith until completely dispersed to form mixture (AB). A clear aqueous solution of skin protecting agent such as dl-panthenol (Phase C) (where present) is mixed with mixture AB. The new mix ABC is then mixed with a mixture of humectant such as a Carbowax, preservative such as a paraben and thickener such as xanthan gum (Phase D) to form mix ABCD. Thereafter preservatives such as one or more parabens, emollients including the acetylated sterol, antioxidant such as dl-alpha-tocopherol, sunscreens and emulsifiers are mixed together and combined with the mixture (ABCD). Then a preservative such as imidazolidinyl urea (Germall 115) is added to the above mix to form the cosmetic formulation of the invention.

A protective daytime lotion/moisturizer in accordance with the invention may be prepared as follows.

An aqueous solution of skin protecting agent such as dl-panthenol and thickener/stabilizer such as magnesium aluminum silicate is mixed with sunscreen, emollient including acetylated sterol, emulsifier, preservative such as one or more parabens, and bodying agent such as steric acid and PEG 20 stearyl ether (Brij 78). After cooling, humectant such as Carobwax, thickener such as xanthan gum and preservative such as a paraben are added. The so-formed mixture is cooled and preservative such as Glydant is added to form the skin care formulation of the invention.

The following Examples represent preferred embodiments of the invention.

EXAMPLE 1

A foundation make-up having the following composition was prepared as described below.

| Ingredient | | Parts by Weight |
|---|---|---|
| Phase A | | |
| Deionized water (diluent) | | 60 |
| Magnesium aluminum silicate (thickener stabilizer) | | 1 |
| Titanium dioxide (water dispersable coloring agent) | | 10 |
| Phase B | | |
| Umber 1985R (67318) | (Iron | 1 |
| Russet C33-2577 (059337) | oxide | 0.4 |
| Yellow 2576 (F12002) | coloring | 1.5 |
| Blue 3516 (63020) (Ultramarine blue) | agents) | 0.001 |
| Talc | | 0.01 |
| Phase C | | |
| dl-Panthenol (skin protecting agent) | | 0.5 |
| Deionized water (diluent) | | 1 |
| Phase D | | |
| Carbowax 400 (PEG 8) (humectant) | | 3 |
| Methyl paraben (preservative) | | 0.2 |
| Xanthan gum (thickener) | | 0.3 |
| Phase E | | |
| Propyl paraben (preservatives) | | 0.2 |
| Butyl paraben | | 0.1 |
| Petrolatum (Emollient) | | 3 |
| Glyceryl tricaprylate/ tricaprate (emollients) | | 7 |
| Phytosterol acetate (acetylated sitosterol-about 56% acetylated campesterol-about 28% acetylated stigmasterol-about 4%) | | 1 |
| Stearic acid (bodying agent) | | 1.5 |
| Glyceryl monostearate (auxiliary emulsifier bodying agent) | | 1 |
| Diethanolamine cetyl phosphate (emulsifier) | | 2.5 |
| Octyl dimethyl p-aminobenzoic acid (sunscreen) | | 2.5 |
| Benzophenone (sunscreen) | | 0.5 |
| dl-alpha-tocopherol (antioxidant) | | 0.1 |
| Phase F | | |
| Deionized water (diluent) | | 1 |
| Germall 115 (6349) (preservative) | | 0.2 |

The ingredients identified as Phase A were mixed for 20 minutes to form a homogeneous mix. The Phase B pigments were added to Phase A with homomixing for 1 hour to disperse the pigments. The Phase C in the form of a clear aqueous solution was mixed with the Phase AB mixture to form mix ABC; mix ABC was then mixed with Carbowax and methyl paraben until a clear solution was formed to which xanthan gum was added with mixing. The resulting uniform mixture was heated 85° C. and the Phase E ingredients were added with mixing and heating to 85° C. The mix was cooled to 45° C. and the phase F ingredients were added and mixed for 10 minutes. The resulting mix was cooled to form a foundation make-up in accordance with the present invention which was found to have improved feel and barrier properties, was naturally compatible with the skin, and had improved skin penetrability.

EXAMPLE 2

A protective daytime lotion/moisturizer having the following composition was prepared as described below.

| Ingredient | Parts by Weight |
| --- | --- |
| Mix A | |
| Deionized water (diluent) | 74 |
| Magnesium aluminum silicate (thickener stabilizer) | 0.5 |
| dl-Panthenol (skin protecting agent) | 1 |
| Mix B | |
| Octyl dimethyl p-aminobenzoic acid (sun screen) | 2 |
| Diisopropyl dimerate (emollient oil) | 4 |
| Propylene glycol dicaprylate/dicaprate (emollient oil) | 8 |
| Propyl paraben (preservative) | 0.1 |
| Stearic acid (opacifier, bodying agent) | 2 |
| Brij 78 (Steareth 20) (emulsifier) | 2 |
| Glyceryl stearate and PEG 100 stearate (emulsifier, thickener) | 2 |
| Phytosterol acetate (emollient) (as described in Ex. 1) | 1 |
| Mix C | |
| Carbowax 400 (PEG 8) (humectant) | 2 |
| Xanthan gum (thickener, stabilizer) | 0.3 |
| Methyl paraben (preservative) | 0.2 |
| Mix D | |
| Glydant (dimethyldimethoyl hydantoin) (preservative) | 0.4 |

Each of Mixes A and B were heated to 75° C. and Mix B was added to Mix A with propeller type mixing while maintaining the 75° C. temperature for 1 hour. The resulting mixture was cooled to 65° C. and Mix C was added. The mixture was then cooled to 50° C. and Mix D was added. Cooling was continued to 30° C. to form the protective daytime lotion/moisturizer of the invention which was found to have improved feel and barrier properties, was naturally compatible with the skin and had improved skin penetrability.

EXAMPLE 3

A soothing make-up having the following composition was prepared as described below.

| Ingredient | Parts by Weight |
| --- | --- |
| Phase A | |
| Deionized water | 48 |
| Veegum R (magnesium aluminum silicate) (thickener) | 1 |
| Phase B | |
| Kaolin 2749 (skin protectant) | 4 |
| Umber 1985R | 0.5 |
| Russet C33-2527 | 0.3 |
| Yellow 2576 | 1 |
| Blue 3516 | 0.01 |
| Phase C | |
| TiO2 water dispersable (90% TiO2, 10% Talc) | 10 |
| Phase D | |
| Alcolec 413S (lecithin and poly- | 1 |

| Ingredient | Parts by Weight |
| --- | --- |
| sorbate 20 and sorbitan laurate and propylene glycol stearate and propylene glycol laurate) | |
| Phase E | |
| Deionized water | 1 |
| dl-Panthenol (skin protectant) | 0.5 |
| Phase F | |
| Carbowax 400 (humectant) | 4.5 |
| Tegosept P (propyl paraben) (preservative) | 0.2 |
| Keltrol F (xanthan gum) (thickener) | 0.2 |
| Phase G | |
| Deionized water | 2 |
| Triethanolamine (96%) (emulsifier) | 1 |
| Phase H | |
| Tegosept P (propyl paraben) (preservative) | .1 |
| Butoben (butyl paraben) (preservative) | .1 |
| Klearol (mineral oil) (emollient) | 5 |
| Miglyol 840 (propylene glycol dicaprylate/tricaprate) (emollient) | 6 |
| Stearic acid (emulsifier, thickener) | 3.5 |
| Tegin 515 (glyceryl monostearate) (auxiliary emulsifier, thickener) | 2.5 |
| Escalol 507 (octyl dimethyl p-amino benzoic acid) (sunscreen) | 2.5 |
| Uvinol M-40 (benzophenone 3) (sunscreen) | 0.5 |
| Phyosterol Acetate (as described in Example 1) | 1 |
| Silicone 225 (emollient) | 1.5 |
| Avocado oil (emollient) | 0.5 |
| PEG-6000 distearate (emulsifier thickener) | 0.2 |
| Vitamin E, dl alpha-tocopherol (antioxidant) | 0.1 |
| Phase I | |
| Deionized water | 0.75 |
| Germall 115 (preservative) | 0.25 |
| Phase J | |
| Carbowax 400 (humectant) | 0.5 |
| Exaltolide (pentadecalactone) (odor masking agent) | 0.5 |

The Phase A ingredients were homomixed for 15 minutes. Thereafter, a mix of the Phase B ingredients were added to the Phase A mixture with mixing for 1 hour.

Phase C was then mixed with Phase AB for ½ hour under slow speed mixing. Phase D was then added to the aforementioned mix with mixing for ½ hour. Phase E was then added and thereafter Phase F was sweep mixed therein for 15 minutes. The so-formed mix was then heated to 75° C. While maintaining the mix at 75° C., Phase G was added. Phase H, heated at 80° C., was then added to the above mix with fast mixing to form an emulsion. The mix was then mixed with moderate speed, cooled to 50° C. and then combined with Phase I and mixed for 5 minutes. Thereafter Phase J was added and the mixture was cooled to 30° C. to form the make-up of the invention. The so-formed make-up of the invention was found to be soothing and noncomedongenic.

What is claimed is:

1. A skin care preparation consisting essentially of at least one acetylated soya bean derived sterol which is acetylated sitosterol, acetylated campesterol or acetylated stigmasterol or a mixture thereof, and is exclusive of acetylated cholesterols, in an amount within the range of from about 0.1 to about 10% by weight which serves as an emollient to impart the above properties to the skin preparation, at least one emulsifier, at least one humectant, at least one diluent, and at least one preservative.

2. The skin care preparation as defined in claim 1 in the form of a cosmetic which is a foundation makeup.

3. The skin care preparation as defined in claim 2 including at least one coloring agent or pigment and at least one sun screen agent.

4. The skin care preparation as defined in claim 1 in the form of a skin moisturizer composition.

5. The skin care preparation as defined in claim 1 wherein the acetylated soya bean derived sterol includes acetylated sitosterol, acetylated campesterol and acetylated stigmasterol.

6. The skin care preparation as defined in claim 5 wherein the mixture of acetylated sterols contains from about 40 to about 80% by weight acetylated sitosterol, from about 10 to about 40% by weight acetylated campesterol, and from about 1 to about 20% by weight acetylated stigmasterol.

7. The skin care preparation as defined in claim 6 wherein the acetylated sitosterol is present in a weight ratio to the acetylated campesterol of from about 2:1 to about 4:1 and the acetylated sitosterol is present in a weight ratio to the acetylated stigmasterol of from about 4:1 to about 40:1.

8. The skin care preparation as defined in claim 1 further including at least one antioxidant, at least one bodying agent, at least one thickener, and at least one skin protecting agent.

9. The skin care preparation as defined in claim 1 including at least one sun screen agent.

* * * * *